(12) United States Patent
Arduengo, III et al.

(10) Patent No.: US 6,177,575 B1
(45) Date of Patent: Jan. 23, 2001

(54) PROCESS FOR MANUFACTURE OF IMIDAZOLES

(75) Inventors: Anthony J. Arduengo, III, Wilmington; Frederick P. Gentry, Jr., Bear, both of DE (US); Prakash K. Taverkere, North Andover, MA (US); Howard E. Simmons, III, Wilmington, DE (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/193,700

(22) Filed: Nov. 17, 1998

Related U.S. Application Data

(60) Provisional application No. 60/089,192, filed on Jun. 12, 1998.

(51) Int. Cl.[7] ........................ C07D 233/58; C07D 233/60
(52) U.S. Cl. ................. 548/335.1; 548/34.1; 548/343.1; 548/343.5; 548/345.1
(58) Field of Search ............................. 548/335.1, 341.1, 548/343.1, 343.5, 345.1

(56) References Cited

U.S. PATENT DOCUMENTS

| | | | | |
|---|---|---|---|---|
| 3,715,365 | * | 2/1973 | Schulze | 548/335.1 |
| 4,074,054 | * | 2/1978 | Christidis et al. | 548/335.1 |
| 4,377,696 | * | 3/1983 | Graf | 548/335.1 |
| 4,450,277 | * | 5/1984 | Graf et al. | 548/335.1 X |
| 4,719,309 | * | 1/1988 | Mesch | 548/335.1 |
| 5,077,414 | * | 12/1991 | Arduengo | 548/335.1 |

FOREIGN PATENT DOCUMENTS

| | | | | |
|---|---|---|---|---|
| 60-67465 | * | 4/1985 | (JP) | 548/335.1 |
| 60-78970 | * | 5/1985 | (JP) | 548/335.1 |
| 60-104072 | * | 6/1985 | (JP) | 548/335.1 |
| 60-105664 | * | 6/1985 | (JP) | 548/335.1 |
| 1-139568 | * | 6/1989 | (JP) | 548/335.1 |
| 1-139569 | * | 6/1989 | (JP) | 548/335.1 |
| 1-149771 | * | 6/1989 | (JP) | 548/335.1 |
| 1-160969 | * | 6/1989 | (JP) | 548/335.1 |
| 3/169865 | | 7/1991 | (JP) | . |
| 4-41477 | * | 2/1992 | (JP) | 548/335.1 |
| 4-82875 | * | 3/1992 | (JP) | 548/335.1 |
| 0058122 | * | 10/1966 | (PL) | 548/335.1 |
| 1747442 | * | 7/1992 | (SU) | 548/335.1 |

OTHER PUBLICATIONS

E. Elvers et al., *Ullmann's Encyclopedia of Industrial Chemistry*, 5th Ed., vol. A13, 661–668, 1989.

M. R. Grimmett, *Comprehensive Heterocyclic Chemistry*, 5, Part 4A, 482–486, 1984.

M. R. Grimmett, *Adv. Heterocyclic Chemistry*, 12, 105–117, 1970.

M. R. Grimmett, *Adv. Heterocyclic Chemistry*, 12, 134, 1970.

* cited by examiner

Primary Examiner—Floyd D. Higel

(57) ABSTRACT

Imidazoles may be manufactured by reacting a glyoxal, ammonia, an aldehyde, and optionally a primary amine, in the presence of a Bronsted acid whose pKa is approximately equal to the pKa of the ammonium cation of the primary amine, or if the primary amine is not present, to the pKa of the ammonium ($NH_4^+$) cation. The reaction may be used to make in relatively high yields a wide variety of imidazoles using relatively inexpensive starting materials. The imidazoles are useful as chemical intermediates.

16 Claims, No Drawings

PROCESS FOR MANUFACTURE OF IMIDAZOLES

This application claims priority benefit of U.S. Provisional Application Ser. No. 60/089,192, filed Jun. 12, 1998.

FIELD OF THE INVENTION

Imidazoles may be made by the reaction of an aldehyde, a glyoxal, ammonium carbonate or bicarbonate, and optionally a primary alkylamine. Imidazoles may also be made by the reaction of an aldehyde, a glyoxal, ammonia, and optionally a primary amine in the presence of a selected Bronsted acid.

TECHNICAL BACKGROUND

Imidazoles are useful as chemical intermediates, for example they are used in the preparation of pharmaceuticals and pesticides. Commercially they are typically made by the condensation of a glyoxal, aldehyde ammonia and optionally an amine, depending on the substituents desired on the imidazole ring, see for example E. Elvers., et al., Ed., Ullmann's Encyclopedia of Industrial Chemistry, $5^{th}$ Ed., Vol. A13, VCH Verlagsgesellschaft mbH, Weinheim, 1989, p. 661–668; M. R. Grimmett in K. T. Potts, Ed., Comprehensive Heterocyclic Chemistry, Vol. 5, Part 4A, Pergamon Press, New York, 1984, p. 482–486; and M. R. Grimmett, Adv. Heterocycl. Chem., Vol. 12, p. 105–117 (1970). However, these condensations often do not give high yields of the desired products, especially when a particular substituted imidazole is desired. Therefore improved syntheses of imidazoles are desired.

As reported in M. R. Grimmett, Adv. Heterocycl. Chem., Vol. 12, p. 1 (1970), formaldehyde and ammonium carbonate, when exposed to actinic radiation having a wavelength of 254 μm, yields a mixture of imidazole, 4-methylimidazole and 4-hydroxymethylimidazole. Such processes are not claimed herein.

Japanese Patent Application 03/169865 describes the preparation of a wide variety of imidazoles using ammonia or an ammonium carbonate as the ammonia source. There is no recognition of the particular use of an ammonium carbonate in the presence of selected amines as described herein.

SUMMARY OF THE INVENTION

This invention concerns, a first process for the manufacture of imidazoles, comprising, contacting in the liquid phase:

(a) ammonium carbonate or ammonium bicarbonate;
(b) a glyoxal of the formula

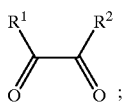

(I)

(c) an aldehyde of formula $R^3CHO$ (II); and
(d) optionally an amine of the formula $R^4NH_2$ (III);
wherein:
$R^1$, $R^2$ and $R^3$ are each independently hydrogen, hydrocarbyl or substituted hydrocarbyl;
$R^4$ is hydrogen, alkyl, or substituted alkyl.

This invention also concerns a second process for the for the manufacture of imidazoles, comprising, contacting in the liquid phase:

(a) an acid of the formula HX;
(b) a glyoxal of the formula

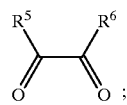

(VI)

(c) an aldehyde of formula $R^7CHO$ (VII);
(d) optionally an amine of the formula $R^8NH_2$ (VIII); and
(e) ammonia
wherein:
$R^5$, $R^6$ and $R^7$ are each independently hydrogen, hydrocarbyl or substituted hydrocarbyl;
$R^8$ is hydrogen, hydrocarbyl, or substituted hydrocarbyl;
X is an anion;
and provided that a pKa of HX is about plus or minus 2 pKa units of a pKa of $R^8NH_3^+$, with the further proviso when (VIII) is not present then a pKa of HX is about plus or minus 2 pKa units of a pKa of $NH_4^+$.

DETAILS OF THE INVENTION

By substituted alkyl is meant an alkyl group substituted with one or more groups which will not interfere with the desired reaction(s) and not render the compound in which they are present substantially unstable. Suitable substituent groups include hydroxyl, ether, and aryl. Herein if not otherwise specified, it is preferred that alkyl groups contain 1–30 carbon atoms.

By hydrocarbyl is meant a chiral or achiral univalent radical containing only carbon and hydrogen. By substituted hydrocarbyl is meant hydrocarbyl substituted with one or more groups which will not interfere with the desired reaction(s) and not render the compound in which they are present substantially unstable. Suitable substituent groups include hydroxyl and ether. Herein if not otherwise specified, it is preferred that hydrocarbyl groups contain 1–30 carbon atoms.

The compounds which are made herein are imidazoles, cyclic compounds having the basic ring structure

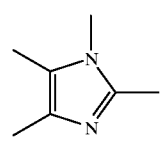

(IV)

From the starting materials of the first process, (I), (II), (III) and ammonium carbonate or bicarbonate, the imidazoles made herein form by the reaction

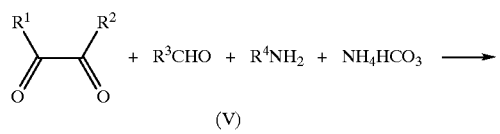

(V)

-continued

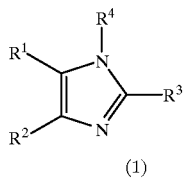

wherein $R^1$, $R^2$, $R^3$ and $R^4$ are as defined above. Water and $CO_2$, not shown in eq. (1), are also "byproducts" of this reaction. The formation of $CO_2$ as the "acidic" byproduct is especially useful, since it is removed from the product as a gas. As will be realized if $R^1$ and $R^2$ are different, their positions may be reversed in (V) and two isomers may be obtained.

Also in equation (1) if $R^4$ is hydrogen, then the amine is ammonia. Ammonia may be added in the form of ammonia or in the form of ammonium carbonate or bicarbonate. Ammonium carbonate has 2 equivalents of ammonia per mole, while ammonium bicarbonate has one equivalent of ammonia per mole. It is preferred the amount of carbon dioxide present is about 5 to about 100 mole percent of first equivalent [i.e., that is as the first mole of ammonia in eq. (1)] of ammonia present, more preferably about 5 to about 95 mole percent of the first equivalent of ammonia present, especially preferably about 10 to about 30 mole percent of the first equivalent of ammonia present, and most preferably about 15 to about 25 mole percent of the first equivalent of ammonia present. In the presence of water ammonia and $CO_2$ form ammonium carbonate and/or bicarbonate, depending on the molar ratio of ammonia to $CO_2$. Included herein within the meaning of ammonium carbonate or bicarbonate is a mixture of ammonia and $CO_2$, or addition of the carbonate or bicarbonate of (III). Since water is formed in the reaction as a byproduct, the carbonate and/or bicarbonate form, even if no water was added to the reaction.

Although the molar ratio of the reactants is not critical, it is preferred to add them to the process mixture in the molar ratios stoichiometrically required by the reaction. Thus the ratio of (I):(II):(III) (if present and $R^4$ is not hydrogen) is preferably about 1:1:1. The ratio of total equivalents of ammonia present (as ammonia and/or ammonium carbonate and/or bicarbonate):(I) is preferably about 1:1 if at least some of $R^4$ is not hydrogen. If (III) is present and all of $R^4$ is hydrogen, the preferred ratio of equivalents of ammonia:(I) is 2:1. Another way of putting this is that the ratio of [the total amount of ammonia equivalents+(III)]:(I) is preferably about 2:1.

In (I) it is preferred that RI and $R^2$ are the same. Preferred groups for $R^1$ and $R^2$ are hydrogen and alkyl containing 1 to 6 carbon atoms, more preferably hydrogen and methyl. The groups $R^1$ and $R^2$ become the groups attached to the 4 and 5 positions of the resulting imidazole ring.

In (II) it is preferred that $R^3$ is hydrogen or alkyl, more preferably hydrogen or alkyl containing 1 to 6 carbon atoms, and especially preferably hydrogen or methyl. $R^3$ becomes the group attached to the 2 position of the resulting imidazole ring.

In (III) it is preferred that $R^4$ is hydrogen, alkyl, or hydroxyalkyl, more preferably hydrogen, alkyl containing 1 to 6 carbon atoms, and 2-hydroxyethyl, especially preferably hydrogen (ammonia) and methyl.

In the first process ammonia derived from ammonium carbonate and/or bicarbonate and any ammonia added becomes the ammonia in the 3 position of the imidazole ring. If (III) is not added or all of $R^4$ is hydrogen, then the ammonia also becomes the nitrogen in the 3 position of the imidazole ring. While less than a stoichiometric amount of (III) in which $R^4$ is not hydrogen may be added, this will usually result in a mixture of products, which is often not desirable.

In the second process herein an imidazole of formula (IV) is also made. The equation which describes this reaction is

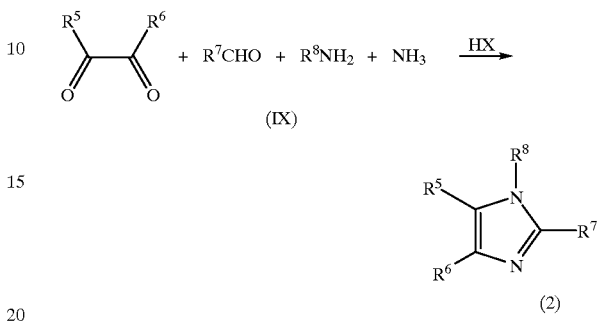

Water, not shown in eq. (2), is also a "byproduct" of this reaction. As will be realized if $R^5$ and $R^6$ are different, their positions may be reversed in (IX) and two isomers may be obtained.

Ammonia and/or (VIII) may be added in the form of the free base of a salt of HX. Of the total of (VIII) present in the reaction, it is preferred that the amount of carbon dioxide present is about 5 to about 100 mole percent of total of (VIII), more preferably about 10 to about 30 mole percent of (VIII) present, and especially preferably about 15 to about 25 mole percent of (VIII) present.

Although the molar ratio of the reactants in the second process is not critical, it is preferred to add them to the process mixture in the molar ratios stoichiometrically required by the reaction. Thus the ratio of (VI):(VII):(VIII):ammonia is preferably about 1:1:1:1. However, if (VIII) is not present then the preferred molar ratio of (VI):(VII):ammonia is preferably about 1:1:2.

In (VI) is preferred that $R^1$ and $R^2$ are the same. Preferred groups for $R^1$ and $R^2$ are hydrogen and alkyl containing 1 to 6 carbon atoms, more preferably hydrogen and methyl. The groups $R^5$ and $R^6$ become the groups attached to the 4 and 5 positions of the resulting imidazole ring.

In (VII) it is preferred that $R^7$ is hydrogen or alkyl, more preferably hydrogen or alkyl containing 1 to 6 carbon atoms, and especially preferably hydrogen or methyl. $R^7$ becomes the group attached to the 2 position of the resulting imidazole ring.

In (VIII) it is preferred that $R^8$ is aryl, substituted aryl, alkyl, or hydroxyalkyl, more preferably phenyl, substituted phenyl, alkyl containing 1 to 6 carbon atoms, and 2-hydroxyethyl.

In the second process ammonia (added as ammonia of the HX salt) becomes the ammonia in the 3 position of the imidazole ring. If (VIII) is not added, then the ammonia also becomes the nitrogen in the 1 position of the imidazole ring. While less than a stoichiometric amount of (VIII) may be added, this will usually result in a mixture of products, which is often not desirable.

In the second process the pKa of the HX added is about ±2 pKa units of the pKa of $R^8NH_3^+$, more preferably about ±1 pKa unit. If (VIII) is not present in the reaction, then the pKa of HX is ±2 pKa units of the pKa of $NH_4^+$, more preferably ±1 pKa unit. The pKa's of the applicable ions are determined by standard methods in water. The values of the pKa's of many ions are available in the literature.

The formula for an acid shown in the second process, HX, is a generalized formula for a Bronsted acid. In fact HX may be an acid such as acetic acid, where X is acetate anion, or phosphoric acid, where X is the dihydrogenphosphate anion.

However HX may also be the dihydrogenphosphate anion if the pKa for dihydrogenphosphate happens to be within the limitations desired. Especially if carried out in aqueous media, a buffer may be employed to maintain the correct pH for the pKa of HX desired.

The HX may also be added in form of an ammonium salt, $NH_4X$, or a salt of (VIII), $R^8NH_3X$. In this instance this type of salt includes both the HX and ammonia or (VIII) needed in the process. At the end of the reaction HX is often present as the free acid and may be recovered by common means, such as distillation.

The temperature at which the first or second process is run is not critical, about $-50°$ C. to about $+150°$ C. being convenient, and about $-20°$ C. to about $50°$ C. being preferred. Many of the reactant combinations are quite active at room (ambient) temperature and so are even more convenient to run there.

The first or second process may be done in aqueous, organic or mixed aqueous-organic media. The use of at least partially aqueous media is advantageous in many instances, since common reactants such as ammonia, formaldehyde, methylamine and other are available at low cost as aqueous solutions.

In the first or second process the order of addition of the reactants is not critical. It is preferred at add all of the ingredients essentially "simultaneously", that is directly in sequence one after the other, and then allow time, if needed to react. However, some cooling may be desirable to control exothermic reaction(s) and/or prevent the escape of volatile ingredients.

By the addition of (I), (II), (VI) and (VII) to the process herein is meant (I), (II), (VI) and (VII) and any chemically active equivalents thereof. For example, (II) or (VII) may be added as an acetal or hemiacetal which hydrolyzes readily to (II) itself. (I) or (VI) may be added as a ketal or hemiketal. If (II) of (VII) is formaldehyde, it may be added as formaldehyde, paraformaldehyde, s-trioxane, etc. If (I) or (VI) is glyoxal itself, it may be added as the trimeric dihydrate.

Because the processes of this invention run quickly, even at ambient temperatures, it is also possible to run the processes in continuous modes, especially when large quantities are desired. In one continuous process the continuous reaction system consists of 4 zones, and any or all of the four zones may be in one or more vessels. The reaction system itself may be constructed of any convenient material that is not significantly attacked or corroded by the reactants or products. This includes stainless steel and glass lined construction. The first zone is a "mixing zone" in which all of the reactants and catalysts are added to and mixed in a continuously flowing system. The initial reactor flow may be initiated by an inert solvent for the reaction when desired. This solvent can be water, a simple alcohol such as methanol, ethanol, propanol or isopropanol, a hydrocarbon such as toluene, xylenes or hexane or any convenient solvent mixture that is chosen to facilitate product isolation, purification or operation of the reactor itself. The solvent should preferably not interfere with the reaction. If not used to initiate the reactor flow, the solvent can also be introduced at any point in the mixing zone. The reactor flow may also be initiated by one of the reactants in the reaction if no additional solvent is desired. For example, the reactor flow could be initiated by the introduction of an aqueous glyoxal solution. After the initiation of the reactor flow by the introduction of the first reactant or a solvent, all remaining reactants are allowed to enter the reactor stream. The addition of the other reactants may be sequential or, in some cases it may be desirable to "pre-mix" two are more of the reactants before they are introduced into the reactor stream in the mixing zone. All reactants are preferably introduced into the "mixing zone" in equal molar ratios (except when an N-unsubstituted imidazole product is desired in which case a second mole equivalent of ammonia is used in place of the primary amine). Depending upon the exact identity and physical properties of the reactants chosen to produce a given target imidazole, the pressure in the mixing zone will preferably be between 0.1 to 20 MPa (1 and 20 atmospheres). The temperature in the mixing zone should be preferably as low as conveniently possible, preferably between $-10°$ and $+40°$ C. and most preferably $10°$ and $20°$ C. The catalyst for the process, e.g. carbon dioxide for 1-alkyl-imidazole syntheses is also introduced in the "mixing zone". Although the catalyst can be introduced at any point in the "mixing zone" it is usually advantageous to add the catalyst near the end of the "mixing zone". The catalyst can be added between a 0.1 and 100 mole ratio relative to the reactants. Generally preferably is as low a level of catalyst as is necessarily to run the reaction in a convenient time. This usually corresponds to between 10 and 100 mole percent catalyst and with carbon dioxide, frequently 20 and 50 mole percent is highly effective. It is also possible to have the catalyst present as co-solvent for the continuous process in which case very high mole ratios of catalysts are present. This is convenient for the synthesis of N-arylimidazoles for which acetic acid may be chosen as the catalyst/co-solvent. After all reactants, the catalyst and any solvent or co-solvent are in contact and well mixed in the mixing zone the reactor stream is conducted into the "reaction zone". The "reaction zone" is constructed so that the reactor stream has a long enough residence time to allow for complete reaction, generally this is less than 10 min. The temperature in the reaction zone may be between $-10°$ and $150°$ C. Preferable is a temperature range between $30°$ and $80°$ C. The pressure in the "reaction zone" may be somewhat higher than that in the mixing zone but is not required to be. The reaction stream is led from the reaction zone into a "de-gassing zone". In the "de-gassing zone" the reaction stream is de-pressurized to remove any dissolved gases such as carbon dioxide that remain in the stream. The reactor stream pressure on exiting the de-gassing zone is usually less than 1 MPa (10 atmospheres). After the de-gassing zone the reactor stream is conducted into a "separation zone" in which the product is separated from solvents, co-solvents, by-products, unused reactants or other impurities. The separation of the product stream may be accomplished by counter-flow extraction from an immiscible solvent in which the product is preferentially soluble. The product separation may also be accomplished by separating two immiscible co-solvents that were present through the reactor process. Variations on such separation schemes are well known to those skilled in the art and may be applied as convenient for a specific process that produces an imidazole with specific physical properties. For example, if toluene was used as a co-solvent with water in the process for a 1-alkylimidazole from glyoxal, formaldehyde, methylamine and ammonia under influence of carbonic acid ($CO_2+H_2O$) catalysis, the toluene stream can be separated from the water stream in the separation zone so that most of the desired N-alkylimidazole product is recovered from the toluene stream. Additional N-alkylimidazole product may also be recovered from the water stream by continuous extraction with fresh toluene. After leaving the separation zone the product stream is conducted into a "purification zone" in which a purification device such as a thin film evaporator may be used to further purify the product.

Yields of imidazoles in these processes are often very high. Most often the first and second processes proceed very rapidly even at moderate temperatures, which is believed due to catalysis by the presence of $CO_2$ or HX. For example at temperatures of about −20° C. to about 50° C. (starting temperature of the ingredients when mixed, and does not include temperature rises due to exothermic reaction), it is preferred that the reaction be essentially complete in about 0.5 to 60 minutes, more preferably about 0.5 to about 30 minutes, and especially preferably about 1 to about 15 minutes. The imidazole compound may be isolated and purified by standard techniques such as distillation and/or crystallization.

In the examples, aqueous formaldehyde contained 37 weight percent formaldehyde, aqueous methylamine contained 40 percent by weight of methylamine, and aqueous glyoxal was 40 weight percent glyoxal. Paraformaldehyde used was 95% pure.

In the Examples the following abbreviations are used:
bp—boiling point
DMSO—dimethylsulfoxide
mp—melting point
RB—round-bottomed
RT—room temperature

EXAMPLE 1

To a 200 ml RB flask was added (in order) 2.79 g (29.0 mmol) of ammonium carbonate, 20 ml water, 4.67 g (58.0 mmol) aqueous formaldehyde, 10 ml water, 4.5 g (58.0 mmol) aqueous methylamine, 10 ml water, 8.42 g (58.0 mmol) aqueous glyoxal and 10 ml water. The solution was refluxed overnight. A small aliquot was taken and analyzed by $^1$H NMR. It showed the presence of 1-methylimidazole as well as a dimethyl substituted imidazolium salt. Removal of volatiles and distillation of the mixture yielded 0.45 g (9.5% yield) of 1-methylimidazole, bp 99–101° C./2.7 kPa.

EXAMPLE 2

To a RB flask cooled to 0–5° C. was added, in order, 94.2 g (1.16 mol) of aqueous formaldehyde, 90 g (1.16 mol) of aqueous methylamine, ammonium carbonate (55.73 g, 0.58 mol), aqueous glyoxal (168.4 g, 1.16 mol) and 700 ml of methanol. The reaction was allowed to stir overnight at RT. Volatiles were removed under vacuum and the mixture vacuum distilled. 1-Methylimidazole, 82.9 g, 87%, bp 99–101° C./2.7 kPa, was obtained.

From a reaction run in a similar way, but at 1/20 of the above scale, distilled 1-methylimidazole had the following NMR spectra. $^1$H-NMR (DMSO-$d_6$, ppm): 3.612 (3H, NMe), 6.87 (1H) and 7.07 (1H) [CH(4,5)], 7.55 [1H, C(2)]. $^{13}$C-NMR (DMSO-$d_6$, ppm): 32.75 (NMe), 120.52 and 128.41 [(CH(4,5)], and 137.94 [CH(2)].

EXAMPLE 3

To a 10 ml flask was added 4.33 mmol of aqueous formaldehyde and 0.2 g of methanol-$d_4$. After cooling to 0–5° C., 4.33 mmol of methylamine in 0.2 g of methanol-$d_4$, 0.208 g (2.17 mmol) ammonium carbonate, 0.3 g of methanol-$d_4$, 0.63 g (4.33 mmol) of aqueous glyoxal solution and finally 0.6 g of methanol-$d_4$. After stirring for 5 min, an aliquot of the solution was transferred to a 5 mm diameter NMR tube. Ten min after the initial mixing a water suppression $^1$H-NMR indicated the reaction was mostly over. Small amounts of starting materials were detected, as were trace amounts of other products. $^1$H-NMR (CD$_3$OD, ppm): (1-methylimidazole) 3.74 (3H, NMe), 6.997 and 7.017 [1H, CH(4,5)], 7.66 [1H, CH(2)]. A small resonance at 3.95 ppm was attributed to 1,3-dimethylimidazolium salt, and small resonances at 7.013, 7.196 and 7.75 were attributed to imidazole.

EXAMPLE 4

To a 200 ml RB flask was added 4.08 g (136 mmol) of paraformaldehyde and 20 ml of methanol. After cooling to 0–5° C., there was added, in order, 7.65 g (129 mmol) i-propylamine, 10 ml methanol, 6.20 g (65 mmol) ammonium carbonate, 10 ml methanol, 9.07 g (43.1 mmol) trimeric glyoxal dihydrate and 25 ml methanol. The reaction was stirred overnight at RT. A small aliquot was removed for NMR analysis. $^1$H-NMR (DMSO-$d_6$, ppm): 1.352 (d, 6H, Me), 4.37 (sept., 1H, CH), 6.86 and 7.19 [1H each, CH(4, 5)], 7.652 [1H, CH(2)]. This indicated 1-methylimidazole was produced in relatively high yield. Volatiles were removed under reduced pressure and the reaction mixture was vacuum distilled to yield 12.16 g (82%) of 1-i-propylimidazole, bp 97–99° C./2.7 kPa.

EXAMPLE 5

To a 200 ml RB flask was added 3.87 g (43 mmol) of trioxane and 20 ml methanol. After cooling to 0–5° C. 10 g (129 mmol) of aqueous methylamine and 10 ml methanol were added over 10 min, followed by 6.20 g (64.5 mmol) of ammonium carbonate, 10 ml methanol, 9.04 g (43 mmol) of trimeric glyoxal dihydrate and 25 ml methanol. After stirring overnight at RT, an aliquot was removed, volatiles were removed from the aliquot on a rotary evaporator and a $^1$H-NMR spectrum obtain. The spectrum indicated that 1-methylimidazole was obtained, but there also appeared to be other products present.

EXAMPLE 6

To a 500 ml RB flask was added 15.67 g (193 mmol) of aqueous formaldehyde and 20 ml methanol. After cooling to 0–5° C., 15 g (193 mmol) of aqueous methylamine and 10 ml methanol were added over 10 min. The 9.28 g (97 mmol) ammonium carbonate and 10 ml methanol were added. Then a solution of 16.78 g (195 mmol) of 2,3-butanedione in 30 ml methanol was added over 10–15 min. After stirring overnight at RT an aliquot was removed, volatiles were removed from the aliquot and an NMR spectrum taken. $^1$H-NMR (DMSO-$_6$, ppm): 1.96 (3H, C—Me), 2.00 (3H, C—Me), 3.408 (3H, NMe), 7.338 [1H, CH(2)]. The product was mostly the desired 1,4,5-trimethylimidazole. Volatiles were removed under reduced pressure from the remaining product mixture and vacuum distilled, yielding 12.8 g (60.3%) of 1,4,5-trimethylimidazole, bp 105–107° C./2.7 kPa.

EXAMPLE 7

To a 500 ml RB flask was added 10 g (123 mmol) of aqueous formaldehyde and 20 ml methanol. After cooling to 0–5° C., 7.53 g (123 mmol) of ethanolamine in 20 ml methanol was added over 10 min. Then 5.91 g (61.5 mmol) of ammonium carbonate, 10 ml methanol, 8.62 g (41 mmol) of trimeric glyoxal trihydrate, and 30 ml methanol were added. After stirring at RT overnight, an aliquot was removed, volatiles removed under vacuum and an NMR spectrum obtained. $^1$H-NMR (DMSO-d$_6$, ppm): 3.633 (t, 2H, NCH$_2$), 3.977 (hept., 2H, OCH$_2$), 6.855 and 7.131 [1H each, CH(4,5)], 7.558 [1H, CH(2)]. Yield of 1-(2-hydroxyethyl)imidazole was 12.67 g, 92% yield. It was crystallized from tetrahydrofuran.

EXAMPLE 8

To a 500 ml RB flask was added 9.28 g (193.2 mmol) of acetaldehyde and 20 ml methanol. After cooling to 0–5° C., 15 g (193.2 mmol) of aqueous methylamine in 30 ml methanol was added over 10 min. Then 9.28 g (96.9 mmol) of ammonium carbonate, 10 ml ethanol, 13.53 g (64.4 mmol) of trimeric glyoxal trihydrate, and 30 ml methanol were added. The solution stirred at 0–20° C. overnight. An aliquot was removed, the volatiles removed from the aliquot and an NMR spectrum taken. $^1$H-NMR (DMSO-d$_6$, ppm): 2.228 (3H, C2Me), 3.496 (3H, NMe), 6,663 and 6.957 [1H each, CH(4,5)]. Volatiles were removed from the product under reduced pressure and the 1,2-dimethylimidazole purified by fractional distillation. Yield 14.2 (77%) of product, bp 102° C./2.7 kPa.

EXAMPLE 9

To a 200 ml RB flask was added 3.95 g (124.9 mmol) of paraformaldehyde. The flask was cooled to –15° C. using a wet ice/salt mixture. The 9.7 g (124.9 mmol) of aqueous methylamine dropwise. Ammonium bicarbonate (9.87 g, 124.9 mmol) was added. Then 18.12 g (124.9 mmol) of aqueous glyoxal was added dropwise. The reaction appeared to proceed almost instantaneously. After stirring 2 h, an aliquot was removed, volatiles removed from it, and an NMR obtained. The NMR spectrum indicated 1-methylimidazole had been obtained in high yield. The reaction mixture was fractionally distilled to give 9.13 g (89%) of 1-methylimidazole, bp 99–101° C./2.7 kPa.

EXAMPLE 10

To a 200 ml RB flask was added 10.13 g (124.9 mmol) of aqueous formaldehyde. The flask was cooled to –12 to –17° C. using a wet ice/salt bath, followed by addition of 9.7 g (124.9 mmol) of aqueous methylamine and 18.12 g (124.9 mmol) of aqueous glyoxal. Then 6.0 g (62.4 mmol) of ammonium carbonate was added. Almost immediately an effervescence was observed (presumably CO$_2$ being formed). After stirring overnight at RT, the water azeotrope was removed under vacuum. A $^1$H NMR of the viscous liquid indicated fairly pure 1-methylimidazole had been formed.

EXAMPLE 11

To a 200 ml RB flask was added 16.45 g (208.1 mmol) of ammonium bicarbonate, 10 g of water, 4.58 g (104.0 mmol) of acetaldehyde, and 15.09 g (104.1 mmol) of aqueous glyoxal. After stirring at RT for 2 h, volatiles were removed on a rotary evaporator and NMR spectra obtained on the resulting yellowish brown solid. $^1$H NMR (DMSO-d$_6$, ppm): 2.253 (s, 3H, Me), 6.848 [s, 2H, CH(4,5)], 8.20–8.40 (very broad, 1H, may be NH). $^{13}$C NMR (DMSO-d$_6$, ppm): 13.69 (Me), 121.19 [CH (4,5)], 143.53 (C2). Minute impurity resonances were observed at 121.5, 135.2 and 165.3. The product was a light yellowish brow solid. Yield 95%. The product was crystallized from tetrahydrofuran/hexane as colorless crystals, mp 140–141° C. $^1$H NMR (DMSO-d$_6$, ppm): 2.235 (3H, Me), 6.817 [2H, CH (4,5)]. 13C NMR (DMSO-d$_6$, ppm): 13.78 (Me), 121.22 [CH (4,5)], 143.395 (C2).

When a similar reaction was performed with ammonium carbonate, and the order of addition was ammonium carbonate, then glyoxal, then acetaldehyde, 2-methylimidazole was obtained. However it was a dark colored liquid and not as pure as obtained above.

EXAMPLE 12

Aqueous formaldehyde (2.27 g, 27.9 mmol) in 20 ml methanol was added to a 500 ml RB flask. Then 4.55 g (27.9 mmol) of 4-trifluoromethylaniline (reported pKa of anilinium salt is 2.6) in 25 ml of methanol was added. A solution of 3.31 g (29.6 weight percent, 27.9 mmol) of aqueous ammonia in 10 ml methanol, and then 4.76 g (28.5 mmol) of 2-nitrobenzoic acid (reported pKa 2.18) in 10 ml methanol were added. After adding 4.05 g (27.9 mmol) of aqueous glyoxal solution dropwise, the mixture was stirred overnight at RT. An aliquot was taken and the solvents removed from the aliquot under vacuum. A $^1$H NMR spectrum was taken in DMSO-d$_6$. Five new resonances were evident in the spectrum, which were consistent with the expected 1-(4-trifluoromethyl-phenyl)imidazole: δ 8.45; three resonances in a multiplet at 7.8–7.9; and 7.2.

EXAMPLE 13

To a 500 ml RB flask at RT was added 100 ml glacial acetic acid, 30 ml aqueous formaldehyde, and 46 ml aqueous glyoxal. The flask was heated to 70° C. in an oil bath, and a solution of 100 ml glacial acetic acid, 30.8 g ammonium acetate, 10 ml water (to solubilize the ammonium acetate), and 56 ml of mesitylamine was added dropwise over a period of about 30 min. The solution was stirred overnight at 70° C. After cooling, the reaction mixture was dripped into a stirred solution of 294 g of NaHCO$_3$ in 3 l of water. A precipitate formed, which was filtered, washed with water, and dried to yield 61.1 g (82%) of a brown-yellow solid. A $^1$H NMR spectrum indicated that the solid was the desired 1-mesitylimidazole.

What is claimed is:

1. A process for the manufacture of an imidazole, comprising, reacting at a temperature of –20° C. to +50° C. in the liquid phase:

(a) ammonium carbonate or ammonium bicarbonate;

(b) a glyoxal of the formula

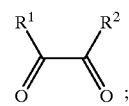

(c) an aldehyde of formula R$^3$CHO (II); and (d) in the absence or the presence of an amine of the formula R$^4$NH$_2$ (III);

wherein:

R$^1$, R$^2$ and R$^3$ are each independently hydrogen, hydrocarbyl or substituted hydrocarbyl;

R$^4$ is hydrogen, alkyl, or substituted alkyl;

and provided that (a), (b), (c) and (d) are added substantially simultaneously to said process.

2. A process for the manufacture of an imidazole, comprising, reacting at a temperature of −20° C. to +50° C. in the liquid phase:
(a) an acid of the formula HX;
(b) a glyoxal of the formula

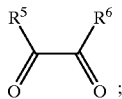

(VI)

(c) an aldehyde of formula $R^7CHO$ (VII);
(d) in the absence or the presence of an amine of the formula $R^8NH_2$ (VIII); and
(e) ammonia
wherein:
$R^5$, $R^6$ and $R^7$ are each independently hydrogen, hydrocarbyl or substituted hydrocarbyl;
$R^8$ is hydrogen, hydrocarbyl, or substituted hydrocarbyl;
X is an anion;
and provided that:
a pKa of HX is about plus or minus 2 pKa units of a pKa of $R^8NH_3^+$;
if (VIII) is not present then a pKa of HX is about plus or minus 2 pKa units of a pKa of $NH_4^+$;
(a), (b), (c) and (d) are added substantially simultaneously to said process.

3. A process for the manufacture of an imidazole, comprising, reacting at a temperature of −20° C. to +50° C. in the liquid phase:
(a) ammonium carbonate or ammonium bicarbonate;
(b) a glyoxal of the formula

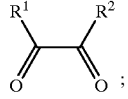

(I)

(c) an aldehyde of formula $R^3CHO$ (II); and
(d) an amine of the formula $R^4NH_2$ (III);
wherein:
$R^1$, $R^2$ and $R^3$ are each independently hydrogen, hydrocarbyl or substituted hydrocarbyl;
$R^4$ is hydrogen, alkyl, or substituted alkyl;
and provided that (a), (b), (c) and (d) are added substantially simultaneously to said process.

4. The process as recited in claim 3 wherein $R^1$ and $R^2$ are each independently hydrogen or methyl, and $R^3$ is hydrogen or alkyl containing 1 to 6 carbon atoms.

5. The process as recited in claim 3 or 4 wherein $R^4$ is alkyl or substituted alkyl.

6. The process as recited in claim 5 wherein $R^4$ is alkyl containing 1 to 6 carbon atoms.

7. The process as recited in claim 3 or 4 wherein a molar ratio of (I):(II):(III):ammonium carbonate or bicarbonate is about 1:1:1:1.

8. The process as recited in claim 1, 3 or 4 wherein a molar ratio of (I):(II):(III) is about 1:1:1.

9. The process as recited in claim 2 wherein $R^5$ and $R^6$ are each independently hydrogen or methyl, and $R^7$ is hydrogen or alkyl containing 1 to 6 carbon atoms.

10. The process as recited in claim 2 or 9 wherein $R^8$ is aryl, substituted aryl, alkyl, or hydroxyalkyl.

11. The process as recited in claim 10 wherein $R^8$ is phenyl, substituted phenyl, alkyl containing 1 to 6 carbon atoms, or 2-hydroxyethyl.

12. The process as recited in claim 2 wherein the pKa of HX is about plus or minus 1 pKa unit of the pKa of $R^8NH_3^+$.

13. The process as recited in claim 2 wherein a molar ratio of (VI):(VII):(VIII):ammonia is about 1:1:1:1.

14. The process as recited in claim 3 wherein:
$R^1$, $R^2$ and $R^3$ are each hydrogen and $R^4$ is 2-hydroxyethyl;
$R^1$, $R^2$ and $R^3$ are each hydrogen and $R^4$ is methyl; or
$R^1$, $R^2$ and $R^4$ are each hydrogen and $R^3$ is methyl.

15. The process as recited in claim 2 wherein:
$R^5$, $R^6$ and $R^7$ are each hydrogen and $R^8$ is 2-hydroxyethyl;
$R^5$, $R^6$ and $R^7$ are each hydrogen and $R^8$ is methyl; or
$R^5$, $R^6$ and $R^8$ are each hydrogen and $R^7$ is methyl.

16. The process as recited in claim 1 or claim 2 wherein the process is run as a continuous reaction system.

* * * * *